US006228626B1

(12) United States Patent
Ichikawa et al.

(10) Patent No.: US 6,228,626 B1
(45) Date of Patent: May 8, 2001

(54) SARCOSINE OXIDASE AND PROCESS FOR PRODUCING THE SAME

(75) Inventors: Toshio Ichikawa; Yasuji Koyama, both of Chiba (JP)

(73) Assignee: Kikkoman Corporation, Noda (JP)

( * ) Notice: Subject to any disclaimer, the term of this patent is extended or adjusted under 35 U.S.C. 154(b) by 0 days.

(21) Appl. No.: 09/457,302

(22) Filed: Dec. 9, 1999

(30) Foreign Application Priority Data

Dec. 14, 1998 (JP) .................................................. 10-354482

(51) Int. Cl.[7] ........................................................ C12N 9/06
(52) U.S. Cl. .................. 435/191; 435/252.33; 435/320.1
(58) Field of Search ............................. 435/183, 41, 191, 435/252.33, 320.1

(56) References Cited

FOREIGN PATENT DOCUMENTS

| 1-034035 | 7/1989 | (JP) . |
|---|---|---|
| 4-094688 | 3/1992 | (JP) . |
| 5-115281 | 5/1993 | (JP) . |
| 6-113840 | 4/1994 | (JP) . |
| 6-065303 | 8/1994 | (JP) . |
| 8-238087 | 9/1996 | (JP) . |

OTHER PUBLICATIONS

Madaras et al. Miniaturized biosensors employing electropolymerized permselective films andtheir use for creatine assays in human serum. Anal Chem. Nov. 1, 1996, vol. 68, pp. 3832–3239.*

Nishiya et al. Alteration of substrate specificity and optimum pH of sarcosine oxidase by random and site–directed mutagenesis. Applied and Environmental Microbiology. 1994, vol. 60, pp. 4213–4215.*

Suzuki et al. Cloning, sequencing, and overexpression in *Escherichia coli* of a sarcosine oxidase–encoding gene linked to the *Bacillus creatinase* gene. Journal of Fermentation and Bioengineering. 1994, vol. 77, pp. 231–234.*

\* cited by examiner

*Primary Examiner*—Nashaat T. Nashed
*Assistant Examiner*—Christian L. Fronda
(74) *Attorney, Agent, or Firm*—Foley & Lardner (57) ABSTRACT

This invention relates to sarcosine oxidase having the following physico-chemical properties: (a) action: oxidatively hydrolyzing 1 mole sarcosine to give 1 mole glycine, 1 mole formaldehyde, and 1 mole hydrogen peroxide; (b) substrate specificity: specific for sarcosine; (c) optimum pH: 7.0–8.0; (d) stable pH range: 7.0–9.5; (e) suitable temperature range for action: 50° C.; (f) thermostability: 55° C. or less; and (g) molecular weight: 44,000 daltons (when estimated roughly from the amino acid sequence of the wild-type), and to a process for producing the sarcosine oxidase, comprising the steps of culturing a microorganism having an ability to produce the sarcosine oxidase and collecting the sarcosine oxidase from the culture are provided.

4 Claims, 5 Drawing Sheets

FIG.1

─□─ 50mM MES Buffer

─◆─ 50mM Phosphate Buffer

─○─ 50mM Tris-HCl Buffer

─△─ 50mM CAPS Buffer

SARCOSINE OXIDASE AND PROCESS FOR PRODUCING THE SAME

FIELD OF THE INVENTION

The present invention relates to sarcosine oxidase which shows a high reactivity under neutral conditions, and to a process for producing the sarcosine oxidase.

BACKGROUND OF THE INVENTION

Sarcosine oxidase is an enzyme which catalyzes a reaction to oxidatively hydrolyze sarcosine to produce glycine, formaldehyde, and hydrogen peroxide. This enzyme can be used for determining creatinine or creatine levels in human sera or urine samples in combination with creatininase or creatinase and therefore is useful as a diagnostic enzyme for a variety of diseases such as hepatic disease.

Conventional sarcosine oxidases have drawbacks such as drastically decreased reactivity under neutral to weakly acidic conditions. Accordingly, they have generally been used under weakly alkaline conditions. See JP-B-1-34035, JP-A-5-115281, JP-A-8-238087, JP-A-6-113840, and JP-A-4-94688. However, when reacted with sera at the optimum pH range, those sarcosine oxidases react well with the substrate but are readily affected by bilirubin, causing errors in assay.

On the contrary, if sarcosine oxidase can be reacted with sera at a pH of approximately 6.5 it will not be affected by bilirubin and thus will not cause such errors. Accordingly, there has always been a need for a sarcosine oxidase which can be used under neutral to weakly acidic conditions.

Moreover, use of such enzyme with an increased reactivity under weakly alkaline conditions (i.e., lower Km value) will be very economical since a smaller amount of the enzyme can provide a sufficient reaction when used as a diagnostic enzyme under normal conditions.

An object of the invention is to provide sarcosine oxidase having a high reactivity under neutral conditions.

Another object of the invention is to provide a process for producing the sarcosine oxidase.

SUMMARY OF THE INVENTION

The present invention is based on a finding that a genetic mutation of a sarcosine oxidase gene derived from Bacillus sp. NS-129 (as disclosed in JP-B-6-65303) gave a mutant sarcosine oxidase which can not only show a higher reactivity (i.e., smaller Km value) than that of a wild-type sarcosine oxidase under weakly alkaline conditions but also keep a relatively higher reactivity under neutral conditions (pH7.0).

Thus, the present invention relates to a sarcosine oxidase which has the following physico-chemical properties:
(a) action: oxidatively hydrolyzing 1 mole sarcosine to give 1 mole glycine, 1 mole formaldehyde, and 1 mole hydrogen peroxide;
(b) substrate specificity: specific for sarcosine;
(c) optimum pH: 7.0–8.0;
(d) stable pH range: 7.0–9.5;
(e) suitable temperature range for action: 50° C.;
(f) thermostability: 55° C. or less; and
(g) molecular weight: 44,000 daltons (when estimated roughly from the amino acid sequence of wild-type).

In an embodiment of the invention, the sarcosine oxidase is obtainable from E. coli JM109 (pSO12 EH) (Accession No. FERM BP-6597) or a variant derived therefrom.

Further, the present invention relates to a process for producing sarcosine oxidase, comprising the steps of culturing a microorganism having an ability to produce the sarcosine oxidase and collecting the sarcosine oxidase from the culture.

In an embodiments of the invention, the microorganism is E. coli JM 109-pSO12 EH, FERM BP-6597, or a variant derived therefrom.

The term "variant" used herein means a mutant strain from E. coli JM109-pSO12EH, FERM BP-6597, which is capable of producing a sarcosine oxidase with the above-described physico-chemical properties.

This specification includes part or all of the contents disclosed in the specification and/or drawings of Japanese Patent Application No. 10-354482, which is a priority-application of the present application.

DETAILED DESCRIPTION OF THE INVENTION

The present invention will be described in detail.

The sarcosine oxidase of the present invention can be obtained, for example, as described below.

First, a recombinant plasmid pSO12 DNA which contains a sarcosine oxidase gene derived from an isolated Bacillus sp. NS-129 strain (Agricultural and Biological Chemistry, 55(5), 1259–1263, 1991) is extracted and purified from E. coli JM109 (pSO12) using QIAGEN (Funakoshi Co., Ltd., Tokyo, Japan).

Vector DNAs which can be used in the present invention are not limited to the above-described plasmid vector DNA but additionally include, for example, bacteriophage vector DNAs and any other plasmid vector DNAs. Particularly, pUC18 (Takara Shuzo Co., Ltd., Kyoto, Japan) is preferred.

Next, any method can be used to obtain a sarcosine oxidase gene which encodes a protein having an amino acid sequence of SEQ ID NO: 1 but with deletions, substitutions or additions of one or more amino acids therein; and having a sarcosine oxidase activity, preferably a relatively high reactivity under neutral to weakly acidic conditions. Examples of such method include random point mutation of the above-described recombinant plasmid DNA, which is generated by using chemical mutagenesis agents such as hydroxylamine or nitrous acid or by PCR methods; a well-known site-directed mutagenesis of the recombinant plasmid DNA wherein site-directed mutation such as substitutions or deletion are generated by using a commercially available kit; and oligonucleotide mutagenesis that is a method comprising the steps of selectively cleaving the recombinant plasmid DNA, removing or adding selected oligonucleotide(s), and then ligating the DNA.

The recombinant DNAs treated as described above can be purified by using, for example, a demineralizaiton column or QUIAGEN (Funakoshi Co., Ltd., Tokyo, Japan) to obtain various recombinant DNAs.

Thus obtained recombinant DNA can be used to obtain a transformant or transfectant which comprises a recombinant DNA containing any fragment of sarcosine oxidase gene by transforming or transfecting, for example, *E. coli* K12, preferably *E. coli* JM109 (Toyobo Co., Ltd., Osaka, Japan), XL1-Blue (Funakoshi Co., Ltd., Tokyo, Japan).

By transformation, for example, a strain which produces sarcosine oxidase having the desired property (i.e., a high reactivity in a neutral pH range) can be obtained from the resultant transformant (which comprises a recombinant plasmid DNA containing a mutated sarcosine oxidase gene) by the following procedure:

Each colony of the obtained transformant is cultured in a liquid medium such as TY medium (supplemented with 50 µg/ml Ampicilin and 1 mM IPTG) to induce various mutant sarcosine oxidases encoded in the recombinant plasmid DNAs. After culture, the culture is subjected to ultrasonication and the crude enzyme-extract solution is determined for its sarcosine oxidase activity. The amount of the crude enzyme solution corresponding to 100 mU is calculated from the obtained activity value. Then, the crude enzyme of the amount corresponding to 100 mU is allowed to react with 0.5 mM sarcosine in 50 mM phosphate buffer (pH7.0). Each variant is extracted and determined for its activity value which is compared with that of the wild-type protein to select a transformant of interest.

By using a transformant or transfectant produced as described above which has an ability to produce sarcosine oxidase showing a high reactivity in a neutral pH range, and preferably using a transformant or transfectant belonging to the genus Escherichia, sarcosine oxidase showing a high reactivity in a neutral pH range can be produced as follows:

A standard solid culture may be used to culture the above-described microorganism although a liquid culture is preferable.

Examples of media for culturing the above-described microorganism include those containing one or more inorganic salts such as potassium dihydrogen phosphate, dipotassium hydrogen phosphate, magnesium sulfate, ferric chloride, ferric sulfate, and manganese sulfate, together with one or more nitrogen sources such as yeast extract, peptone, meat extract, corn steep liquor, and exudate of soy bean or wheat koji. Saccharine materials, vitamines, and the like may be added if required.

An initial pH of the medium may be adequately adjusted to a pH of 7–9. A microorganism may be preferably cultured at a temperature of 30–42° C. and preferably about 37° C., for a period of 6–24 hours by, for example, submerged aeration culture, shaking culture or stationary culture. After culture, sarcosine oxidase may be collected from the culture by usual enzyme collection methods.

Cells are separated from the culture by filtration, centrifugation, and the like, and then washed. Preferably, sarcosine oxidase may be collected from the cells. In this case, the cells per se may be used. Alternatively, sarcosine oxidase may be preferably collected from the cells by, for example, disruption of cells using any means such as ultrasonic disrupter, Frenchpress, Diner Mill, and the like, lysis of the cell-walls using a cell wall-lysing enzyme such as lysozyme, or extraction of an enzyme from the cells with surfactants such as TritonX-100.

Usual methods for purifying an enzyme may be used to isolate sarcosine oxidase from the crude enzyme solution obtained as described above. For example, ammonium sulfate precipitation, organic solvent precipitation, ion exchange chromatography, gel filtration chromatography, absorption chromatography and electrophoresis may be used alone or in combination.

Physico-chemical properties of the sarcosine oxidase of the present invention are as follows:

1) Action

This enzyme oxidatively hydrolyzes 1 mole sarcosine oxidase to produce 1 mole glycine, 1 mole formaldehyde, and 1 mole hydrogen peroxide;

2) Substrate specificity

This enzyme is specific for sarcosine;

3) Optimum pH

Figure 1:
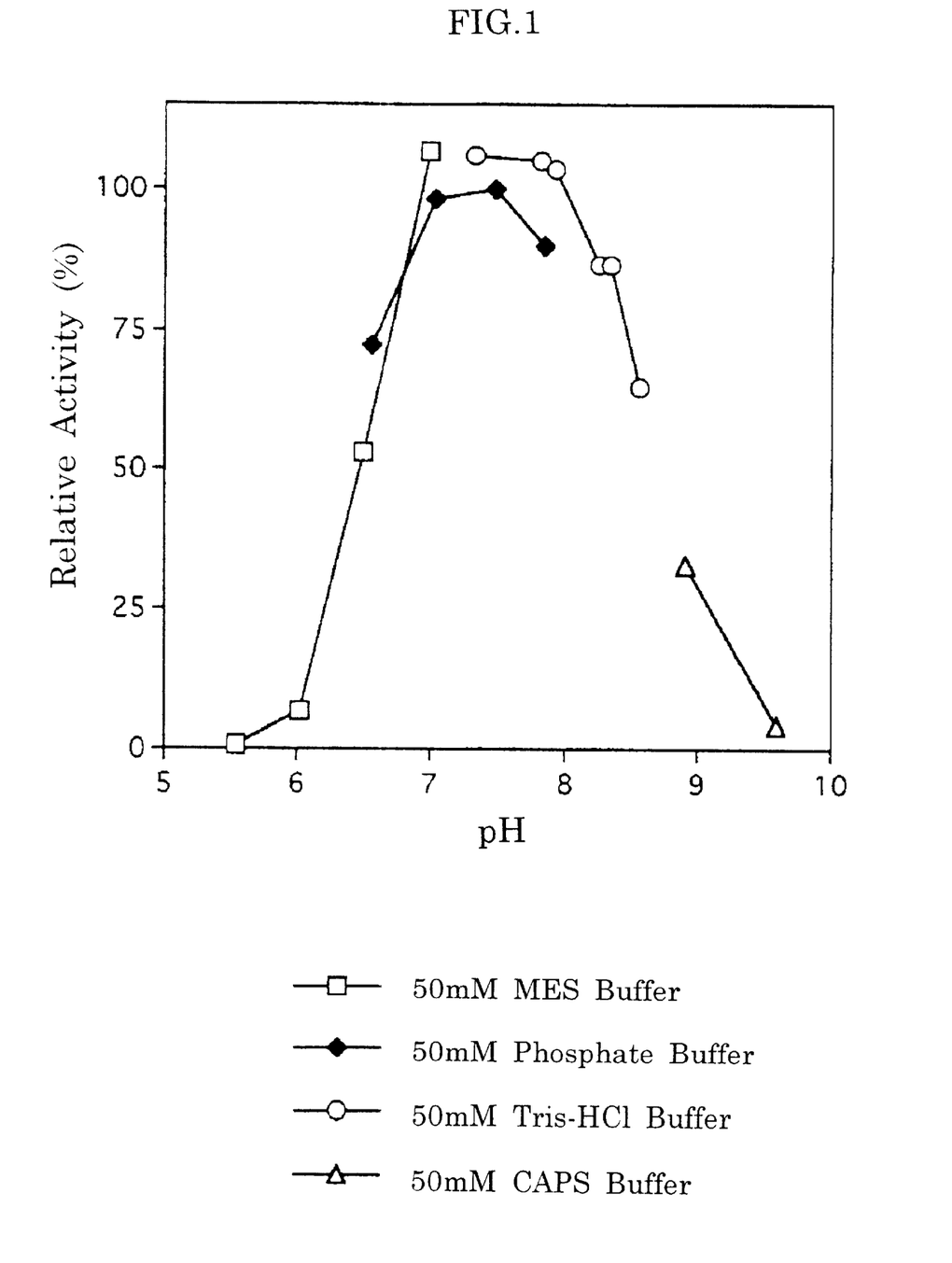
FIG. 1 is a diagram showing the optimum pH of the enzyme of the present invention.

The relative activity of the enzyme was determined at 37° C. for 10 minutes under various pH conditions in 50 mM MES buffer (pH5.5–7.0), 50 mM phosphate buffer (pH6.5–8.0), 50 mM Tris-HCl buffer (pH7.0–8.5) and 50 mM CAPS buffer(pH9.0–9.5). The relative activities are shown in FIG. 1 from which the optimum pH of the enzyme was proved to be in a range of pH 7.0–8.0.

4) Suitable temperature range for action

Figure 2:
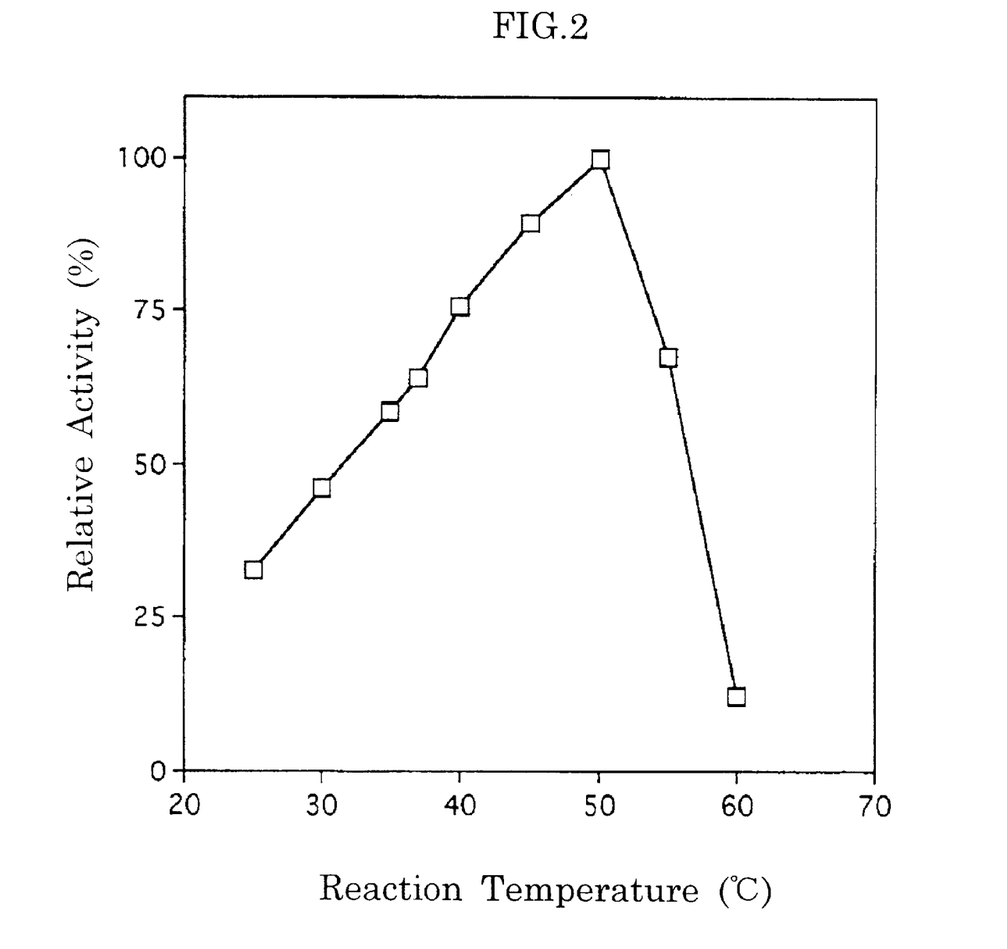
FIG. 2 is a diagram showing the appropriate temperature range for reaction of the enzyme of the present invention.

The reactivity of the enzyme was determined at various temperatures in an reaction solution comprising the same compositions as that to be used in the assay described below. The results are shown in FIG. 2 from which the appropriate temperature for reaction of the enzyme was proved to be 50° C.

5) Stable pH range of the Enzyme

Figure 3:
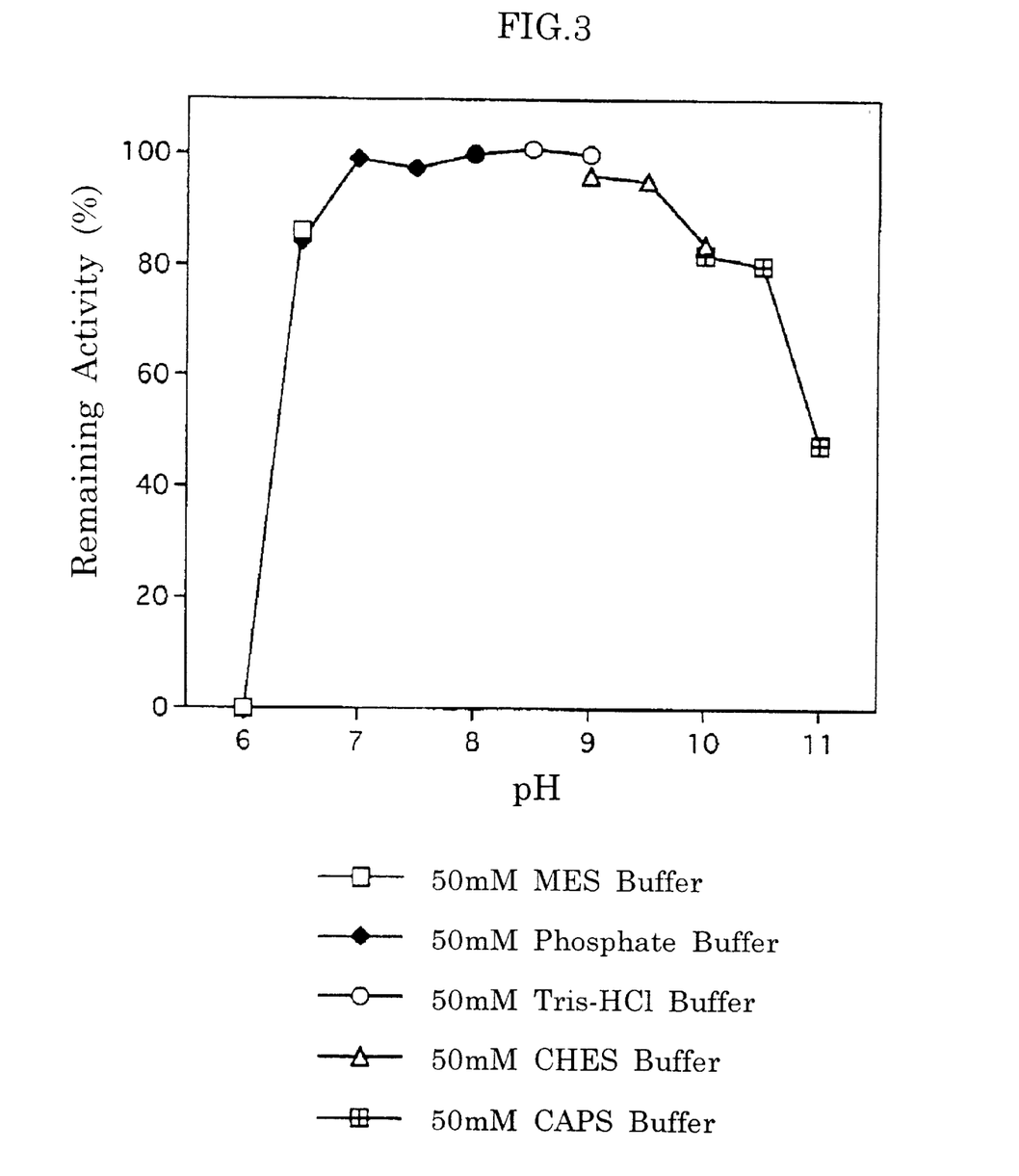
FIG. 3 is a diagram showing the suitable pH range for stability of the enzyme of the present invention.

The pH stability of the enzyme was tested at 20° C. for 20 hours at pH 6.0–11.0 in 50 mM MES buffer (pH6.0–8.0), 50 mM phosphate buffer (pH6.0–8.0), 50 mM Tris-HCl buffer (pH8.0–9.0), 50 mM CHES buffer (pH9.0–10.0) and 50 mM CAPS buffer(pH10.0–11.0). The results are shown in FIG. 3 from which the stable pH range was proved to be pH 7.0–9.5.

6) Thermo-stability

Figure 4:
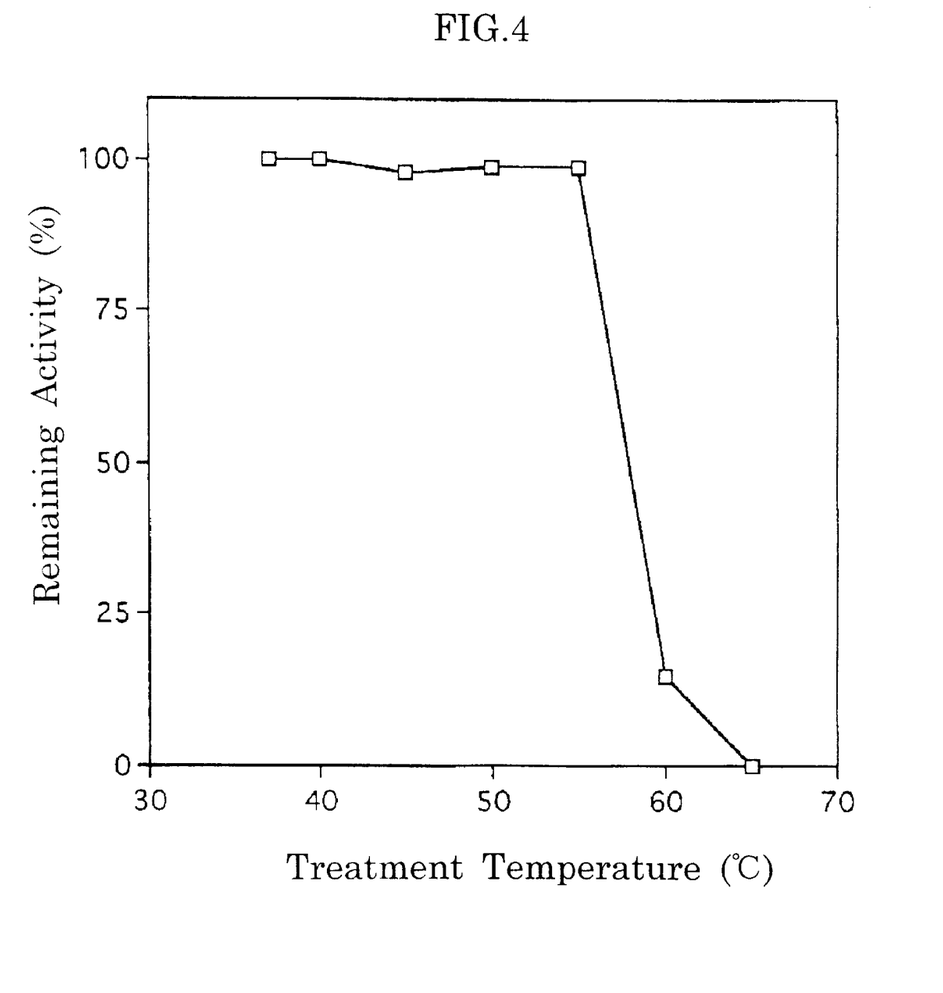
FIG. 4 is a diagram showing the thermostability of the enzyme of the present invention.

The thermo-stability of the enzyme was tested in 50 mM phosphate buffer (pH7.7) at various temperatures for 10 minutes. The results are shown in FIG. 4 from which the enzyme was proved to be stable at a temperature up to about 55° C.

7) Enzyme assay 0.25M phosphate buffer (0.1 ml, pH7.7), 0.2 M sarcosine solution (0.3 ml) and the enzyme solution with an appropriate concentration (0.1 ml) were mixed and reacted at 37° C. for 10 minutes. Then, 1.0 N acetic acid solution (0.5 ml) was added to the mixture to stop the reaction. To the mixture was added 3 ml of acetylacetone color-developing solution (acetyl-acetone, 0.2%(v/v) and diammonium hydrogenphosphate, 10% (w/v) ) (pH6.5) to develop the color at 37° C. for 40 minutes. The absorbance was determined at 410 nm by spectrophotometer. Then, the yield of the enzyme was estimated from the calibration curve of formaldehyde prepared beforehand. The amount of the enzyme which produces 1 µmole of formaldehyde per minute at 37° C. was defined as 1 unit.

8) Km Value

The Km value of the enzyme was determined using the assay as described above. The Km value was estimated to be approximately 3.5mM (for sarcosine) from Lineweaver-Burk plot.

9) Reactivity under Neutral Condition

Figure 5:
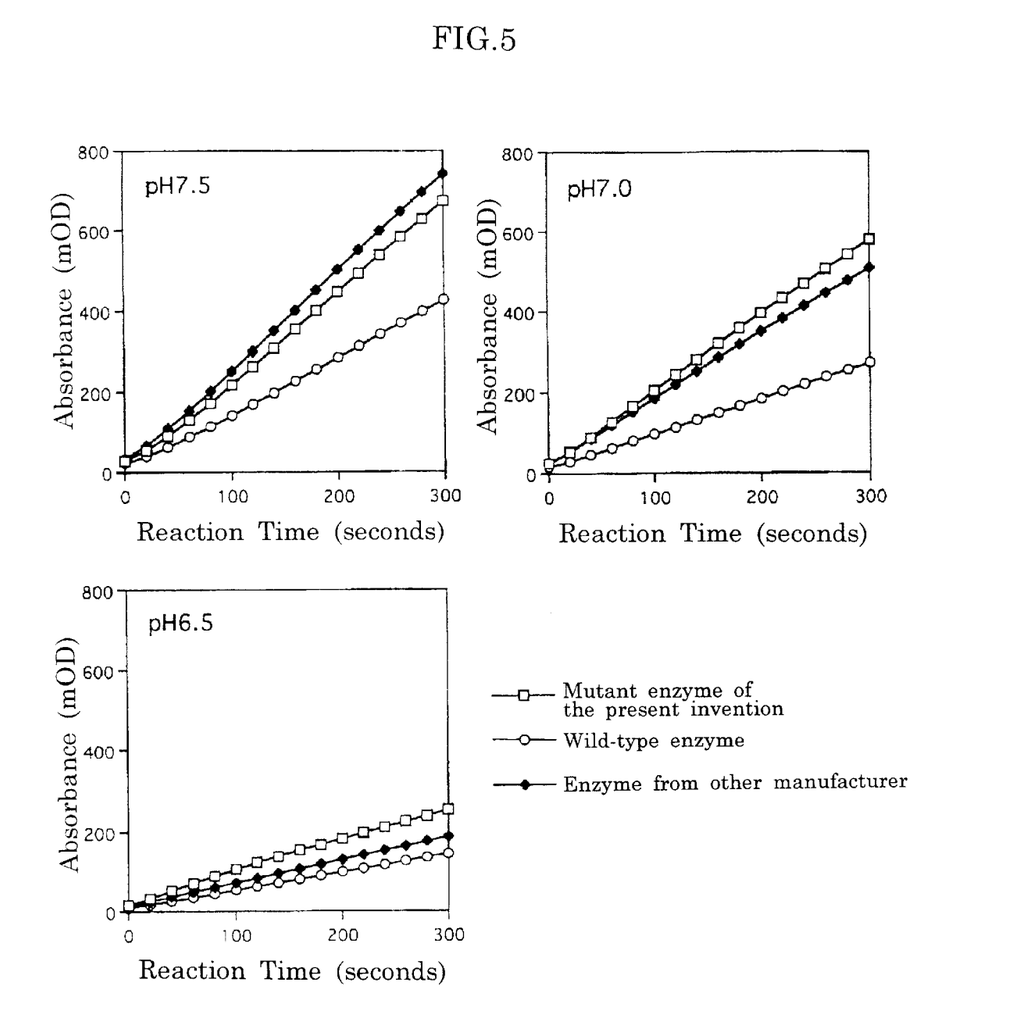
FIG. 5 is a diagram showing the comparison of the reactivity among the mutant enzyme of the present invention, the wild-type enzyme, and a certain sarcosine oxidase commercially available from other manufacturer.

Since the mutant enzyme shows a higher reactivity than other sarcosine oxidases under a neutral condition (pH 7.0), the reactivity of 30 mU/ml enzyme with 0.5 mM substrate (sarcosine) was compared with that of a commercially available sarcosine oxidase which had Km value almost equivalent to and high homology to the enzyme. The results are shown in FIG. 5. The present mutant enzyme shows relatively lower reactivity than that of the commercially available sarcosine oxidase, but extremely higher reactivity than that of the wild-type, under weakly alkaline conditions while it showed higher reactivity under neutral to weakly acidic conditions (pH7.0–6.5).

10) Molecular Weight

This enzyme has a molecular weight of 44,000 daltons (when estimated roughly from the amino acid sequence of the wild-type)

EXAMPLES

Particular examples of the present invention will be described below.

Example 1

(1) Preparation of Recombinant Plasmid pSO12 DNA

E. coli JM109 (pSO12) (Agricultural and Biological Chemistry, 55 (5), 1259–1263, 1991) was inoculated into 20 ml of TY medium (1% Tryptone, 0.5% yeast extract, 0.25% NaCl, pH 7.5) and grown by shaking culture at 37° C. for 18 hours. The culture was centrifuged at 6,000 rpm for 10 minutes to collect the cells. Recombinant plasmid pSO12 DNA was extracted and purified from the cells using QIAGEN tip-100 (Funakoshi Co., Ltd., Tokyo, Japan) to give 70 μg of recombinant plasmid pSO12 DNA.

(2) Mutagenesis

Two μg of the recombinant plasmid DNA obtained above was used to transform XL1-RED (STRATAGENE Co., USA) (which is more likely to generate error in plasmid replication and consequently more likely to generate mutation) in accordance with the method of D. M. Morrison (Method in Enzymology, 68, 326–331, 1979) to give about 1,500 colonies of the transformant among which 500 colonies were all inoculated and grown in 20 ml of TY medium at 37° C. for 18 hours by shaking culture. The culture was centrifuged at 6,000 rpm for 10 minutes to collect the cells. Then, plasmid pSO12 was extracted and purified from the cells using QIAGEN tip-100 (Funakoshi Co., Ltd., Tokyo, Japan) to give 70 μg of mutant recombinant plasmid pSO12 DNA of which 5 μg was used to transform E. coli JM109 strain (Toyobo Co., Ltd., Osaka, Japan) in accordance with the method of D. M. Morrison (supra) to give about 2,000 transformants containing mutated plasimds. E. coli JM109-pSO12 EH, FERM BP 6597, which produces sarcosine oxidase with high reactivity at a neutral pH range was obtained by screening under a neutral condition (pH7.0) in accordance with the method described in (3) below.

(3) Screening of a Variant Showing a High Reactivity at a Neutral pH Range

First, each colony of the transformants obtained above was cultured in a liquid medium, 2 ml of TY medium (supplemented with 50 μg Ampicilin and 1 mM IPTG) and various sarcosine oxidases encoded in the plasmids were induced to be produced. Next, the culture was subjected to ultrasonic disruption. The resulting crude enzyme-extract solution was determined for its reactivity at pH7.0. The obtained value was used to calculate an amount of the crude enzyme solution corresponding to 100 mU. The crude enzyme solution of an amount corresponding to 100 mU was allowed to react with 0.5 mM of substrate (sarcosine) to determine its reactivity. Similarly, each of other variants was extracted and its reactivity was compared to that of wild-type sarcosine oxidase. A variant which satisfies the object of the present invention was selected, and a sarcosine oxidase which showed a high reactivity at a neutral pH range was obtained from the selected variant E. coli JM109-pSO12 EH. E. coli JM109-pSO12 EH was deposited under the terms of the Budapest Treaty with the National Institute of Bioscience and Human-Technology, Agency of Industrial Science and Technology (Higashi 1-1-3, Tsukuba-shi, Ibaraki-ken, Japan) as FERM BP-6597 on Dec. 11, 1998.

Example 2

The variant obtained above, i.e. E. coli JM109-pSO12 EH, FERm BP 6597, was grown in 100 ml of 1 mM isopropyl-β-D-galactoside-containing TY medium (1% Tryptone, 0.5% yeast extract, 0.25% NaCl, pH7.5) dispensed in Sakaguchi flasks for 16 hours by shaking culture, and then flame-inoculated into 20 L of similarly prepared TY medium in a 30 L culture vessel. After inoculated, the E. coli strain was grown at 450 rpm, 20 L air/min, and 37° C. for about 20 hours.

After culture, the cells were collected from 20 L of the culture by microzer (PW-303, available from Asahi Chemical Industry Co., Ltd., Osaka, Japan), washed in 20 mM phosphate buffer (pH7.5), and suspended in 10 L of the same phosphate buffer.

Twenty gram of lysozyme (in 50 mM phosphate buffer, pH7.5, 100 ml) and 1 L of 0.55M EDTA (pH8.0) were added to 10 L of the cell suspension described above, mixed, left at 30° C. overnight and then added with 500 ml of 5% protamine solution (pH8.0) in droplets with stirring to remove nucleic acids. The aqueous phase was dialyzed against 10 mM phosphate buffer (pH8.0) (hereinafter referred to as "buffer A").

After about 3 kg (by wet weight) of DEAE-cellulose was added to and mixed with about 28 L of the dialyzate to allow sarcosine oxidase to be adsorbed thereon, the DEAE-cellulose was washed with buffer A containing 5% glycerin and 0.05% 2-mercaptoethanol. Then, sarcosine oxidase was eluted with 0.5 M KCl-containing buffer A prior to ultrafiltration and concentration.

What is claimed is:

1. An isolated mutant sarcosine oxidase derived from randomly mutating the DNA sequence encoding the wild-type sarcosine oxidase of Bacillus sp. NS-129 of SEQ ID NO: 1, wherein the mutant sarcosine oxidase has the following physico-chemical properties:
   (a) action: oxidatively hydrolyzing 1 mole sarcosine to give 1 mole glycine, 1 mole formaldehyde, and 1 mol hydrogen peroxide;
   (b) substrate specificity: specific for sarcosine;
   (c) optimum pH: 7.0–8.0;
   (d) stable pH range: 7.0–9.5;
   (e) suitable temperature for action: 50° C.; and
   (f) thermostability: 55° C. or less for at least 10 minutes.

2. The sarcosine oxidase of claim 1 wherein the sarcosine oxidase is obtainable from *E. coli* JM109-pSO12EH, FERM BP 6597.

3. A process for producing sarcosine oxidase, comprising the steps of culturing a microorganism having an ability to produce the sarcosine oxidase of claim 1 and collecting the sarcosine oxidase from the culture.

4. The process of claim 3 wherein the microorganism is *E. coli* JM109-pSO12EH, FERM BP 6597.

* * * * *

SEQUENCE LISTING

<160> NUMBER OF SEQ ID NOS: 1

<210> SEQ ID NO: 1
<211> LENGTH: 387
<212> TYPE: PRT
<213> ORGANISM: Bacillus sp.

<400> SEQUENCE: 1

| Met | Ser | Thr | His | Phe | Asp | Val | Ile | Val | Val | Gly | Ala | Gly | Ser | Met | Gly |
|-----|-----|-----|-----|-----|-----|-----|-----|-----|-----|-----|-----|-----|-----|-----|-----|
| 1 | | | | 5 | | | | | 10 | | | | | 15 | |

Met Ala Ala Gly Tyr Tyr Leu Ala Lys Gln Gly Val Lys Thr Leu Leu
                20                  25                  30

Val Asp Ser Phe Asp Pro Pro His Thr Asn Gly Ser His His Gly Asp
        35                  40                  45

Thr Arg Ile Ile Arg His Ala Tyr Gly Glu Gly Arg Glu Tyr Val Pro
    50                  55                  60

Phe Ala Leu Arg Ala Gln Glu Leu Trp Tyr Glu Leu Lys Glu Thr
65                  70                  75                  80

His His Lys Ile Phe Thr Gln Thr Gly Val Leu Val Tyr Gly Pro Lys
                85                  90                  95

Gly Gly Ser Ala Phe Val Ser Glu Thr Met Glu Ala Ala Asn Ile His
                100                 105                 110

Ser Leu Glu His Glu Leu Phe Glu Gly Lys Gln Leu Thr Asp Arg Trp
            115                 120                 125

Ala Gly Val Glu Val Pro Asp Asn Tyr Glu Ala Ile Phe Glu Pro Asn
130                 135                 140

Ser Gly Val Leu Phe Ser Glu Asn Cys Ile Gln Ala Tyr Arg Glu Leu
145                 150                 155                 160

Ala Glu Ala His Gly Ala Thr Val Leu Thr Tyr Thr Pro Val Glu Asp
                165                 170                 175

Phe Glu Val Thr Glu Asp Leu Val Thr Ile Lys Thr Ala Lys Gly Ser
                180                 185                 190

Tyr Thr Ala Asn Lys Leu Val Val Ser Met Gly Ala Trp Asn Ser Lys
            195                 200                 205

Leu Leu Ser Lys Leu Asp Val Glu Ile Pro Leu Gln Pro Tyr Arg Gln
210                 215                 220

Val Val Gly Phe Phe Glu Cys Asp Glu Ala Lys Tyr Ser Asn Asn Ala
225                 230                 235                 240

His Tyr Pro Ala Phe Met Val Glu Val Glu Asn Gly Ile Tyr Tyr Gly
                245                 250                 255

Phe Pro Ser Phe Gly Gly Ser Gly Leu Lys Ile Gly Tyr His Ser Tyr
            260                 265                 270

Gly Gln Gln Ile Asp Pro Asp Thr Ile Asn Arg Glu Phe Gly Ala Tyr
            275                 280                 285

Pro Glu Asp Glu Ala Asn Leu Arg Lys Phe Leu Glu Gln Tyr Met Pro
290                 295                 300

Gly Ala Asn Gly Glu Leu Lys Lys Gly Ala Val Cys Met Tyr Thr Lys
305                 310                 315                 320

Thr Pro Asp Glu His Phe Val Ile Asp Leu His Pro Lys Tyr Ser Asn
                325                 330                 335

Val Ala Ile Ala Ala Gly Phe Ser Gly His Gly Phe Lys Phe Ser Ser
            340                 345                 350

Val Val Gly Glu Thr Leu Ala Gln Leu Ala Thr Thr Gly Lys Thr Glu
            355                 360                 365

His Asp Ile Ser Ile Phe Ser Leu Asn Arg Asp Ala Leu Lys Lys Glu
        370                 375                 380

Ala Val Lys
385